United States Patent
Chen et al.

(10) Patent No.: US 8,710,221 B2
(45) Date of Patent: Apr. 29, 2014

(54) PROCESS AND INTERMEDIATES FOR PREPARING LAPATINIB

(71) Applicants: Yung-Fa Chen, Tainan (TW); Julian Paul Henschke, Tainan (TW); Xiaoheng Zhang, Changshu (CN); YiJing Chen, ChiaYi (TW); ChunFang Xu, Changshu (CN); Yong Mu, Changshu (CN)

(72) Inventors: Yung-Fa Chen, Tainan (TW); Julian Paul Henschke, Tainan (TW); Xiaoheng Zhang, Changshu (CN); YiJing Chen, ChiaYi (TW); ChunFang Xu, Changshu (CN); Yong Mu, Changshu (CN)

(73) Assignee: Scinopharm Taiwan, Ltd., Tainan (TW)

( * ) Notice: Subject to any disclaimer, the term of this patent is extended or adjusted under 35 U.S.C. 154(b) by 0 days.

(21) Appl. No.: 14/030,705

(22) Filed: Sep. 18, 2013

(65) Prior Publication Data

US 2014/0024829 A1    Jan. 23, 2014

Related U.S. Application Data

(63) Continuation-in-part of application No. 13/582,875, filed as application No. PCT/CN2011/000493 on Mar. 23, 2011, now Pat. No. 8,563,719.

(60) Provisional application No. 61/316,425, filed on Mar. 23, 2010.

(51) Int. Cl.
  *C07D 239/72*    (2006.01)
  *C07D 405/04*    (2006.01)

(52) U.S. Cl.
  CPC .................................. *C07D 405/04* (2013.01)
  USPC ........................................................ 544/293

(58) Field of Classification Search
  CPC .................................................... C07D 405/04
  See application file for complete search history.

(56) References Cited

U.S. PATENT DOCUMENTS

| 6,713,485 B2 | 3/2004 | Carter et al. |
| 6,727,256 B1 | 4/2004 | Carter et al. |
| 7,157,466 B2 | 1/2007 | McClure et al. |

FOREIGN PATENT DOCUMENTS

| AU | 2005203303 A1 | 8/2005 |
| WO | WO2006/066267 A2 | 6/2006 |
| WO | WO2009/042613 A1 | 4/2009 |
| WO | WO-2009/079541 A2 | 6/2009 |
| WO | WO-2010/017387 A2 | 2/2010 |

OTHER PUBLICATIONS

English Translation of Search Report of the Taiwan Counterpart Patent Application No. TW100109970.
Organic Process Research & Development 2005, 9, 198-205.
Organic Process Research & Development 2003, 7, 733-742.
Petrov, K. G., Optimization and SAR for dual ErbB-1/ErbB-2 tyrosine kinase inhibition in 6-furanylquinazoline series, Bioorganic & Medicinal Chemistry Letters, Jun. 13, 2006, vol. 16, pp. 4686-4691.
Organic Process Research & Development 2009, 13, 429-433.

*Primary Examiner* — Taofiq Solola
*Assistant Examiner* — John S Kenyon
(74) *Attorney, Agent, or Firm* — Enshan Hong; Kent H. Cheng; VLP Law Group LLP

(57) ABSTRACT

A compound of formula (X):

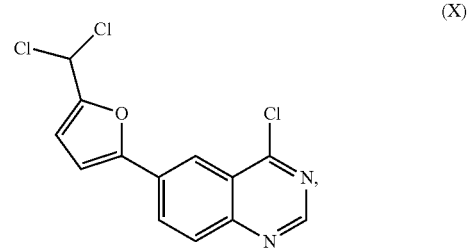

which can be used as an intermediate to make lapatinib or its pharmaceutically acceptable salt.

8 Claims, 4 Drawing Sheets

PROCESS AND INTERMEDIATES FOR PREPARING LAPATINIB

CROSS REFERENCE TO RELATED APPLICATIONS

This application is a continuation-in-part of U.S. patent application Ser. No. 13/582,875 which is a U.S. national phase application based on PCT/CN2011/000493 filed on Mar. 23, 2011, which claims priority from U.S. Provisional Application No. 61/316,425 filed on Mar. 23, 2010. The entire content of the related applications is incorporated herein as reference.

BACKGROUND OF THE INVENTION

1. Field of the Invention

The present invention is related to a process of making lapatinib, salts and novel intermediates thereof Lapatinib has the structural formula (I) and chemical name N-[3-chloro-4-[(3-fluorophenyl) methoxy]phenyl]-6-[5-[(2-methylsulfonylethylamino)methyl]-2-furyl]quinazolin-4-amine.

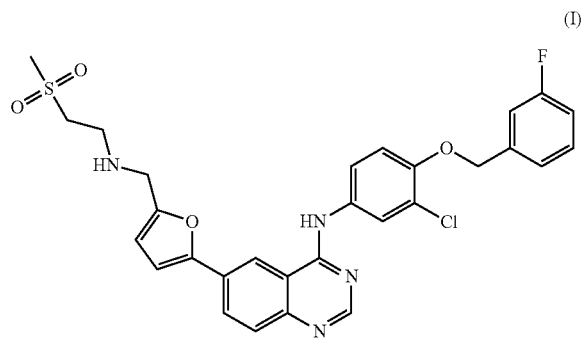 [SMILES: CS(=O)(=O)CCNCc1ccc(-c2ccc3ncnc(Nc4ccc(OCc5cccc(F)c5)c(Cl)c4)c3c2)o1]

(I)

Lapatinib is an orally administered small-molecule epidermal growth factor receptor (EGFR) tyrosine kinase inhibitor, used in the form of ditosylate salt to treat advanced or metastatic breast cancer and other solid tumors which were treated by Anthracyclines, Taxanes and Trastuzumab (Herceptin®). Lapatinib ditosylate was approved by the FDA in 2007 and the EMEA in 2008 and is marketed by GlaxoSmithKline (GSK) under the trade name of Tykerb® in the USA and Tyverb® in Europe.

There is a need for an improved process of making lapatinib and its pharmaceutically acceptable salts.

SUMMARY OF THE INVENTION

In accordance with one aspect of the present invention, a process for preparing lapatinib or its pharmaceutically acceptable salt comprising converting a compound of formula (X):

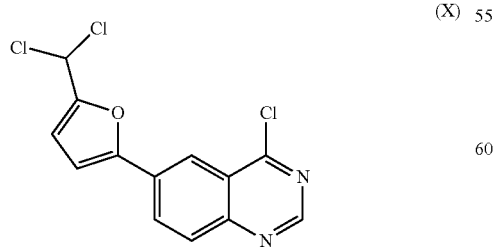

(X)

to lapatinib or its pharmaceutically acceptable salt.

Another aspect of the present invention is a compound of formula (X) as shown above or its salts, preferably an HCl salt. The compound of formula (X) is stable and suitable for industrial production. In addition, the compound of formula (X) can provide higher selectivity and yield for the process of preparing lapatinib.

In accordance with yet another aspect of the present invention, the compound of formula (X) is synthesized by reacting a compound of formula (IX)

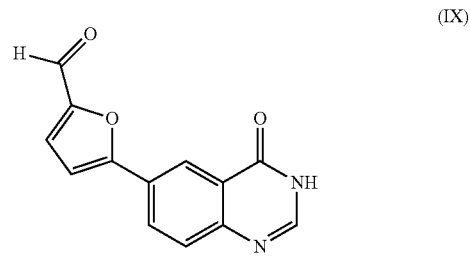 [SMILES: O=Cc1ccc(-c2ccc3nc[nH]c(=O)c3c2)o1]

(IX)

with $SOCl_2$ in the presence of dimethylformamide (DMF).

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Figure 1:
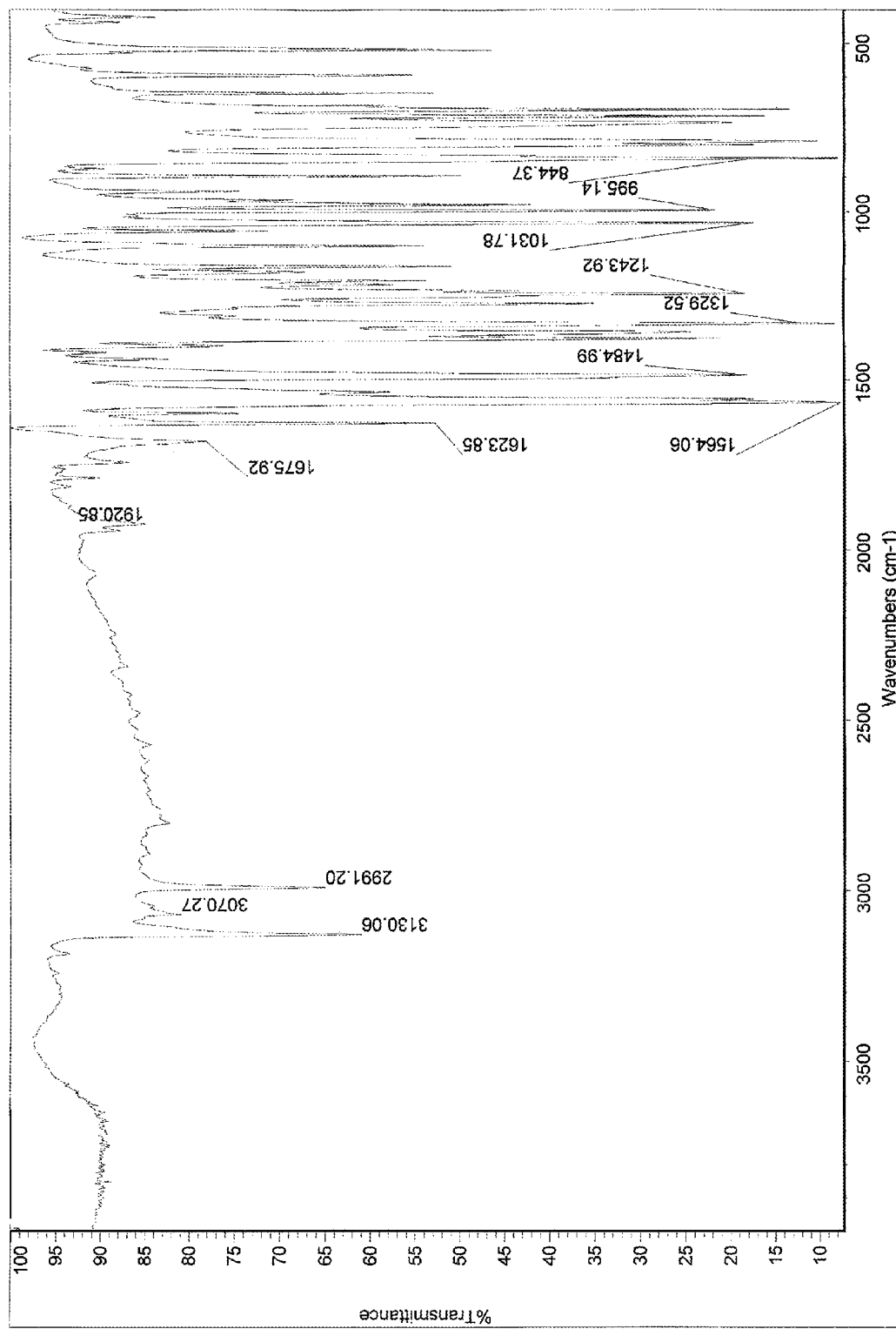
FIG. 1 shows the IR spectrum of the compound of formula (X).

In one embodiment, lapatinib is produced by i) reacting the compound of formula (X)

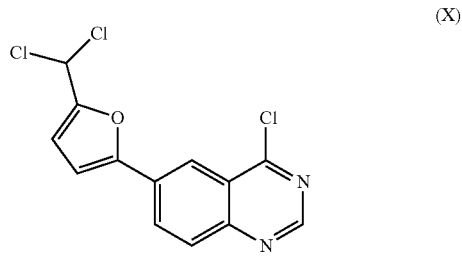 [SMILES: Clc1ncnc2ccc(-c3ccc(C(Cl)Cl)o3)cc12]

(X)

with 3-chloro-4-(3-fluorobenzyloxy)aniline (VII)

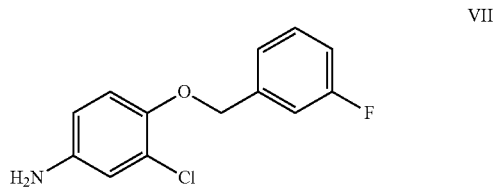 [SMILES: Nc1ccc(OCc2cccc(F)c2)c(Cl)c1]

VII in a solvent with or without a base to produce the compound of formula (IV) or its salt

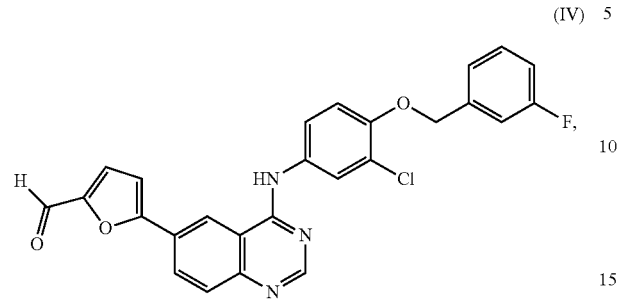

(IV)

and ii) reductively aminating the compound of formula (IV) or its salt with 2-(methylsulfonyl)ethanamine (VIII) or its salt (e.g., (VIII).HCl) to provide lapatinib.

The solvent in step i) can be tetrahydrofuran (THF), acetonitrile (MeCN), N,N-dimethylformamide (DMF), N,N-dimethylacetamide (DMAC), 1,3-dimethyl-2-imidazolidinone (DMI), N-methylpyrrolidone (NMP), or tetramethylurea (TMU) and is preferably selected from THF, DMF, and MeCN, each having water content of no more than 100 ppm as determined by Karl-Fischer (KF) titration, most preferably MeCN with a KF value of no more than 100 ppm.

In another embodiment, (X) is reacted with the compound of formula (VII) in a polar solvent such as DMF, DMAC, DMI, NMP or TMU to give a homogeneous reaction solution. After the reaction is complete, water is added to precipitate the (IV).HCl. The (IV).HCl is then isolated by filtration.

The novel intermediate of the compound of formula (X) provide high yield for the process of preparing lapatinib.

EXAMPLES

The following examples are provided for illustrating, but not limiting, the present invention.

Example 1

Synthesis of 5-(4-oxo-3,4-dihydroquinazolin-6-yl) furan-2-carbaldehyde (IX)

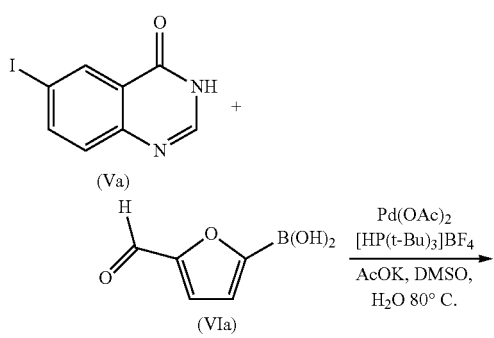

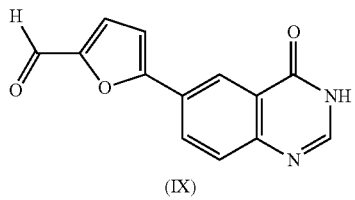

(IX)

A 5:2 v/v solvate mixture of Dimethyl sulfoxide (DMSO) and H$_2$O (1400 mL) was degassed for 30 min at ambient temperature using nitrogen. Under an atmosphere of nitrogen, 5-formylfuran-2-ylboronic acid ((VIa); 26.8 g, 193 mmol) was added into this mixture and dissolved. [HP(t-Bu)$_3$]BF$_4$ (840 mg, 2.94 mmol) and palladium acetate (Pd(OAc)$_2$, 680 mg, 2.94 mmol) was added and the mixture was stirred at ambient temperature for 20 min. Then, potassium acetate (AcOK, 18.8 g, 192 mmol) was added into the reactor and was stirred for 20 min. 6-Iodoquinazolin-4(3H)-one ((Va); 40 g, 147 mmol) was added. Then the reaction mixture was heated to 80±5° C. (internal temperature). Upon completion of the reaction (HPLC), the reaction mixture was hot-filtered, then hot water (400 mL, 80±5° C.) was added into the filtrate. This was slowly cooled to 0-15° C. (solid started to precipitate at 70° C. (internal temperature)) and was then filtered. The filter cake was washed with H$_2$O (80 mL), then with MeCN (60 mL), and dried in vacuo at 60±5° C. for 6 h to provide 5-(4-oxo-3,4-dihydroquinazolin-6-yl)-furan-2-carbaldehyde ((IX); 34.6 g, 144 mmol) with 99.7% HPLC purity in 97.6% HPLC yield. 1H NMR (300 MHz, d6-DMSO): δ 7.47 (d, J=3.8 Hz, 1H), 7.69 (d, J=3.8 Hz, 1H), 7.77 (d, J=8.6 Hz, 1H), 8.17 (s, 1H), 8.27 (dd, J=8.6, 2.1 Hz, 1H), 8.52 (d, J=2.1 Hz, 1H), 9.66 (s, 1H); $^{13}$C NMR (75 MHz, CDCl$_3$): δ 110.5, 122.6, 123.9, 126.0, 127.5, 129.0, 131.4, 147.1, 150.1, 152.7, 157.6, 161.2, 178.8; ESI-MS, Pos: [M+H]$^+$ m/z 241; IR (cm$^{-1}$): 1713, 1671, 1604, 1462; m.p.: 267° C.

Example 2

Synthesis of compound of formula (X)

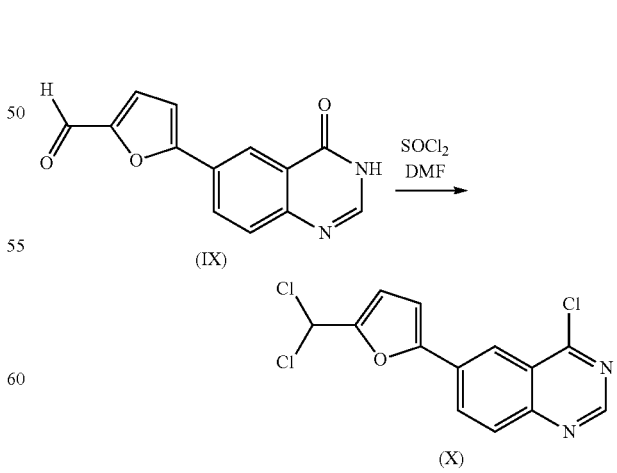

DMF (8.7 mL, 116 mmol, 0.16 eq.) was added to a compound of formula (IX) (174.0 g, 725 mmol, 1.0 eq.) in thionyl chloride (1740 mL) and the mixture was stirred and heated to 55-60° C. for 1 hour then increased temperature to 80° C. and stirred at this temperature for not less than 2 hours. Excess thionyl chloride was removed by distillation under reduced pressure and the residue was azeotropically-distilled with toluene (1740 mL) twice (controlled temperature at 80-90° C.) to become about 400 mL. Toluene (350 mL) and n-heptane (1400 mL) were added to the residue and stirred at ambient temperature for not less than 2 hours. The batch was filtered and the wet cake was washed with n-heptane (500 mL) and dried at 40±5° C. under vacuo for 10 hours to afford bright yellow solid compound of formula (X) (212 g, 83.5% yield with 91.8% purity). 1H NMR (400 MHz, CDC13) δ: 9.07 (s, 1H), 8.55 (d, J=1.8 Hz, 1H), 8.30 (dd, J=8.8, 1.8 Hz, 1H), 8.18 (d, J=8.8 Hz, 1H), 6.92 (d, J=3.5 Hz, 1H), 6.81 (s, 1H), 6.76 (d, J=3.5 Hz, 1H).

Figure 2:
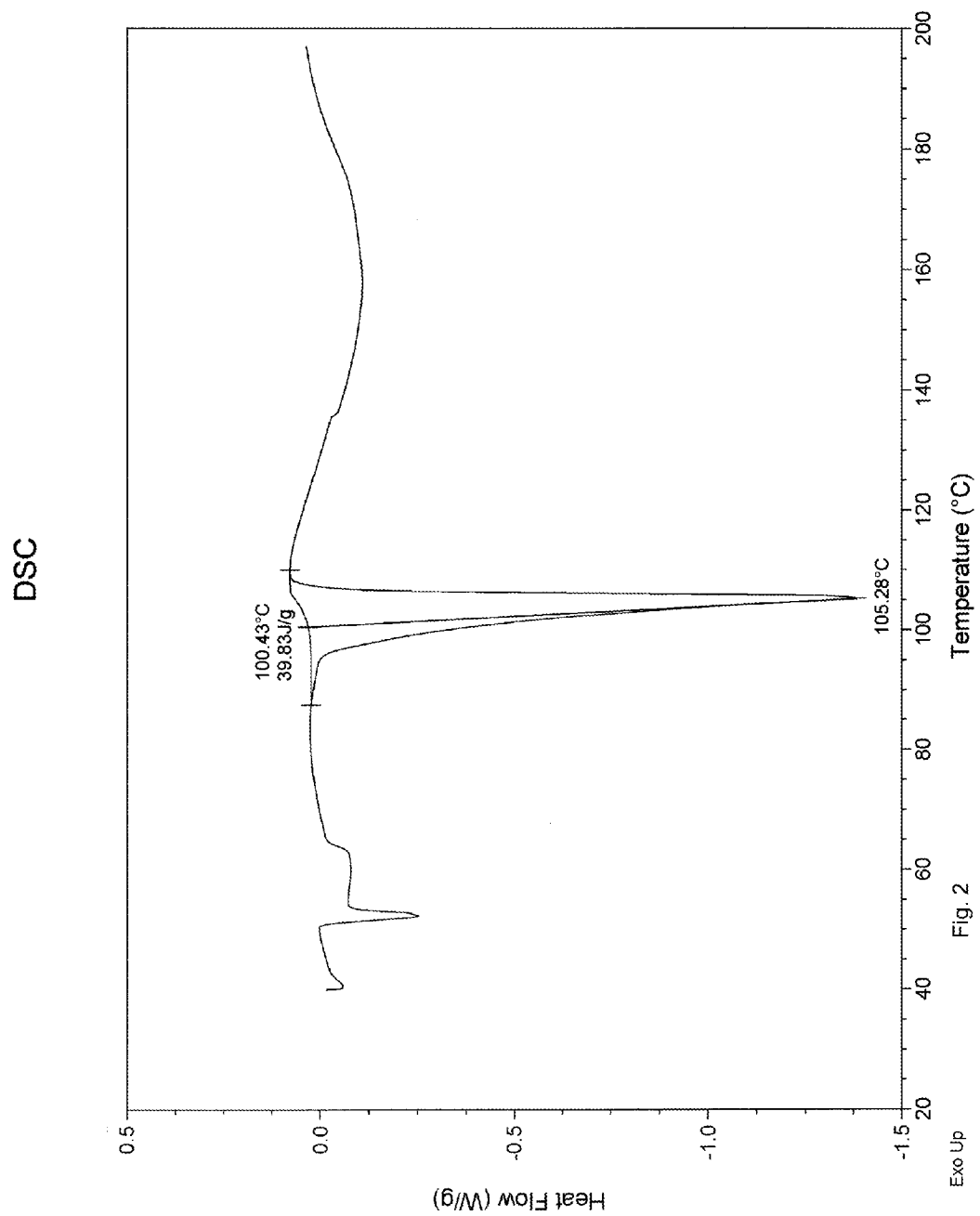
FIG. 2 shows the DSC of the compound of formula (X).
Figure 3:
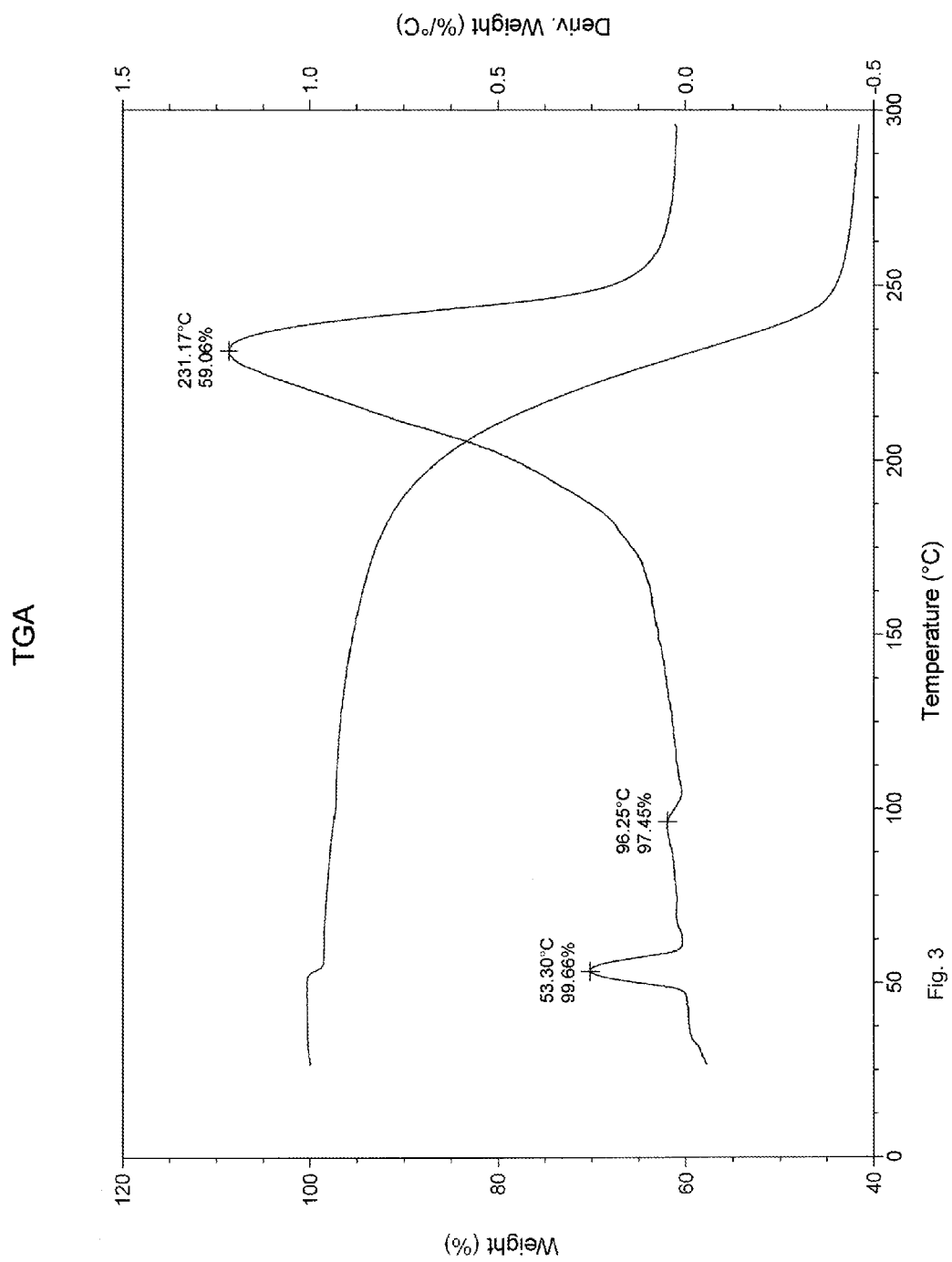
FIG. 3 shows the TGA of the compound of formula (X).
Figure 4:
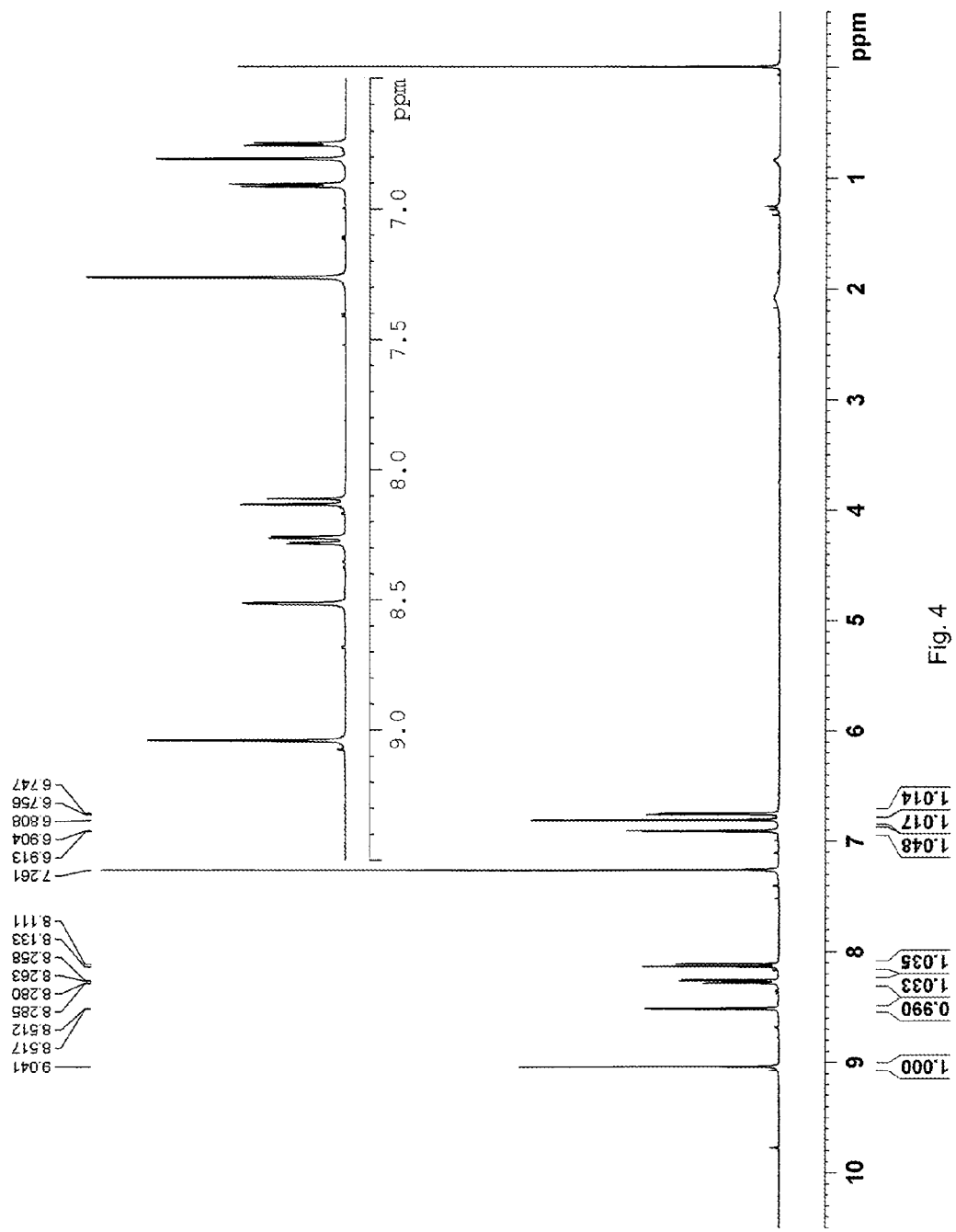
FIG. 4 shows the $^1H$ NMR spectrum of the compound of formula (X).

The IR spectrum, DSC, TGA, and 1H NMR of the compound of formula (X) are respectively shown in FIGS. 1-4. The conditions used by DSA, TGA, IR, and NMR tests are provided below respectively:

DSC: DSC-TA Q2000; condition: 40° C. to 200° C. (10° C./min)

TGA: TGA-TA Q500; condition: Room temperature to 300° C. (10° C./min)

IR: Nicolet FT-IR Avatar 360; condition: KBr Pellet

NMR: Bruker AVANCE III 400 MHz; condition: in CDCl$_3$, 298 K

Example 3

Synthesis of Compound of Formula (IV)

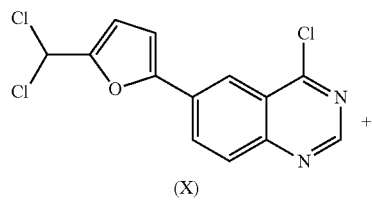

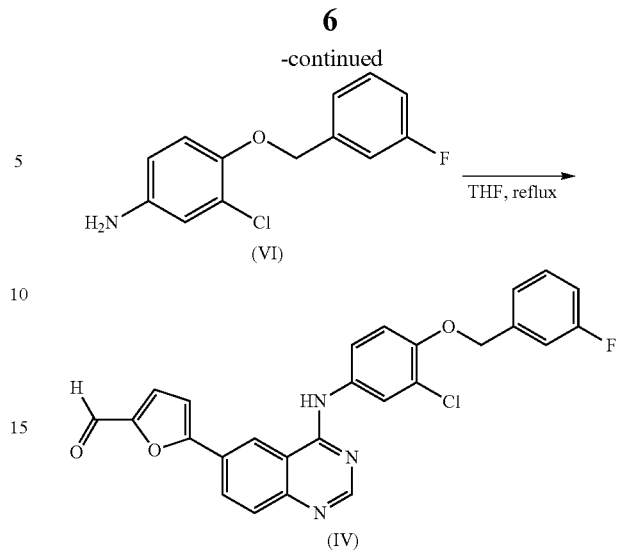

3.0 g of compound of formula (X) and THF (24 mL) were added into flask, and then heated to reflux. 3-chloro-4-(3-fluorobenzyloxy) benzenamine ((VII), 2.4 g) THF (12 mL) solution was added dropwise. The reaction mixture was kept stirring and reflux for 1 hour. Then H$_2$O (3 mL) was added and kept reflux for 0.5 h. The mixture was cooled to 25° C. in water bath. The mixture was alkalized to pH=8-9 with 30% K$_3$PO$_{4aq}$. The organic phase was separated and heated to reflux, and then n-heptane (12 mL) was added dropwise. The mixture was cooled to ambient temperature and stirred for 2 hours at ambient temperature. The mixture was filtered, and the filter cake was washed with THF/heptane (1:1, 4.5 mL) and was then dried under vacuum at 80±5° C. for 4 h to give 3.6 g (IV) with 96.4% HPLC purity.

Example 4

Synthesis of N-(3-chloro-4-(3-fluorobenzyloxy)phenyl)-6-(5-((2-(methylsulfonyl) ethylamino)methyl) furan-2-yl)quinazolin-4-amine ditosylate (lapatinib ditosylate)

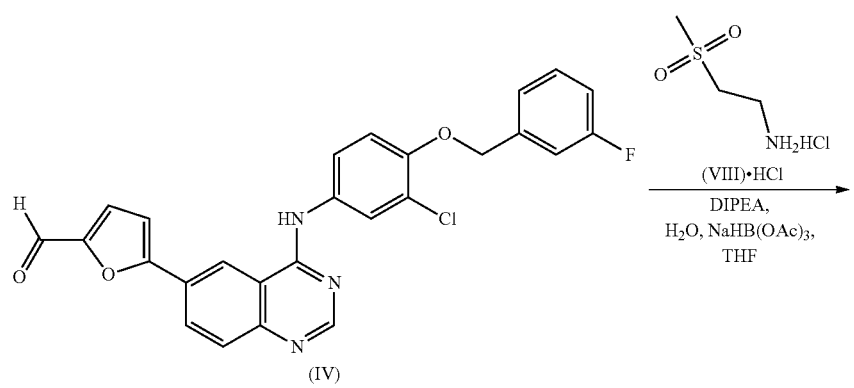

-continued

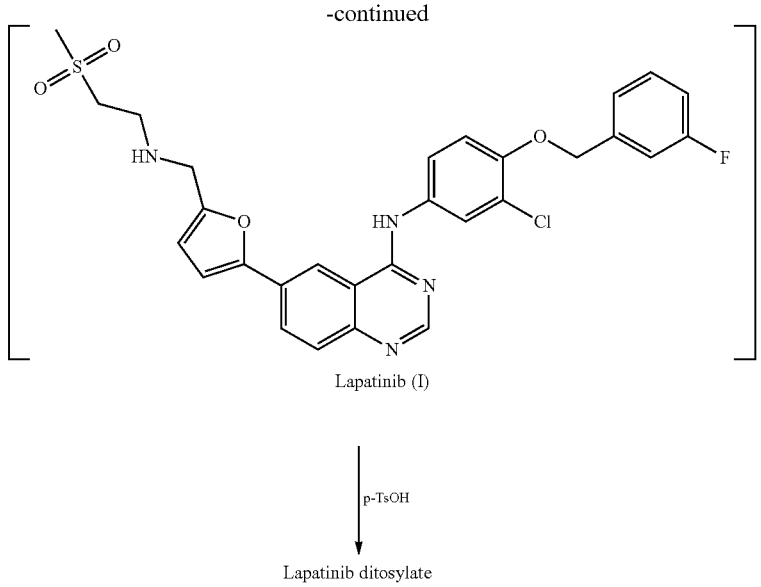

Lapatinib (I)

↓ p-TsOH

Lapatinib ditosylate

To a suspension of 2-(methylsulfonyl)ethanamine hydrochloride (1.3 g, 8.1 mmol) and compound of formula (IV) (3.0 g, 6.3 mmol) in THF (60 mL) was added DIPEA (4.7 mL). After stirred at ambient temperature for 0.5 hours, sodium triacetoxyborohydride (4.0 g, 24.3 mmol) was added and the mixture was stirred at 20±5° C. (external temperature) until HPLC showed the completion of the reaction. Reaction mixture was quenched with $H_2O$ (9 mL, 3 P) in ice-water bath to keep $T_{in}$ <25° C. The organic phase was washed with 10% aqueous $NH_4Cl$ (6 mL), filtered, treated with p-TsOH (4.8 g, 25.2 mmol) and heated to reflux for 2 h. The mixture was cooled to ambient temperature and stirred for 15 h at ambient temperature. The mixture was filtered, and the filter cake was washed by 1:1 (v/v) $THF/H_2O$ (4.5 mL), dried under vacuum at 80±5° C. for 6 h to give crude lapatinib ditosylate (3.4 g, HPLC purity: 95.2%). Lapatinib ditosylate $^1H$ NMR (300 MHz, $d_6$-DMSO): δ 11.41(s, 2H), 9.33 (s, 3H), 9.04 (d, J=1.3 Hz, 2H), 8.93 (s, 2H), 8.41 (dd, J=8.8, 1.6 Hz, 2H), 7.91 (d, J=2.6 Hz, 2H), 7.54-7.41 (m, 9H), 7.37-7.27 (m, 6H), 7.25 (d, J=3.4 Hz, 2H), 7.22-7.13 (m, 2H), 7.08 (dd, J=8.4, 0.6 Hz, 8H), 6.87 (d, J=3.5 Hz, 2H), 5.29 (s, 4H), 4.46 (s, 4H), 3.65-3.51 (m, 4H), 3.51-3.38 (m, 4H), 2.26 (s, 12H).

Lapatinib ditosylate was converted to its free base form, lapatinib, by washing the THF solution of lapatinib ditosylate with aqueous NaOH followed by concentration to obtain lapatinib solid. Lapatinib: $^1H$ NMR (300 MHz, $d_6$-DMSO): δ 2.98 (t, J=6.75 Hz, 1H), 3.04 (s, 1H), 3.29 (t, J=6.6 Hz, 1H), 3.83 (s, 1H), 5.28 (s, 1H), 6.50 (d, J=3.0 Hz, 1H), 7.08 (d,J=3.3 Hz, 1H), 7.20 (m, 1H), 7.33 (m, 4H), 7.48 (m, 1H), 7.76 (m, 1H), 7.80 (d, J=9 Hz, 1H), 8.04 (d, J=2.75 Hz, 1H), 8.17 (dd, J=8.7 Hz, J=1.8 Hz, 1H), 8.56 (s, 1H), 8.75 (d, J=1.8 Hz, 1H).

Example 5a

Purification of Lapatinib Ditosylate

Lapatinib ditosylate (5.0 g, 5.4 mmol, 96.5% HPLC purity with the maximum individual impurity at 0.8%) was dissolved in DMSO (10 mL) at 70° C. (internal temperature). MeCN (10 mL) was added dropwise into the mixture at 70-80° C. (internal temperature) and was stirred at this temperature for 1 h. Over a 4 h period the mixture was cooled to room temperature. MeCN (30 mL) was added dropwise, and the mixture was stirred for 1 h, then filtered and washed with MeCN (10 mL). The filter cake was dried under vacuum at 60° C. for 16 h to give 4.0 g lapatinib ditosylate as crystalline Form 1 (as disclosed in U.S. Pat. No. 7,157,466 B2) with 99.6% HPLC purity in 78% HPLC yield.

Example 5b

Purification of Lapatinib Ditosylate

Lapatinib ditosylate (3 g, 3.25 mmol, 99.3% HPLC purity was dissolved in DMF (18 mL) at 80° C. and stirred for 1 hour. The mixture was hot-filtered. MeCN (18 mL) was added into the filtrate at 80° C. The temperature was cooled to 70° C. and crystal precipitated. The mixture was kept at 70° C. for 1 h and then 60° C. for 1 h. The mixture was further cooled to 0° C. and stirred for 2 h. The crystals of lapatinib ditosylate were isolated by filtration and were dried at 40° C. under vacuum overnight. Lapatinib ditosylate (2.5 g, 2.70 mmol, 83% yield) with 99.9% HPLC purity was obtained. XRPD analysis indicated that this was Form 2 as disclosed in WO 2009/079541 A1.

The invention is not limited by the embodiments described above which are presented as examples only but can be modified in various ways within the scope of protection defined by the appended patent claims.

We claim:

1. A process for preparing lapatinib or a pharmaceutically acceptable salt thereof comprising converting a compound of formula (X):

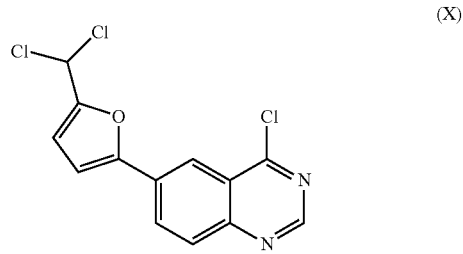 [SMILES: Clc1ncnc2ccc(-c3ccc(C(Cl)Cl)o3)cc12]

(X)

to lapatinib:

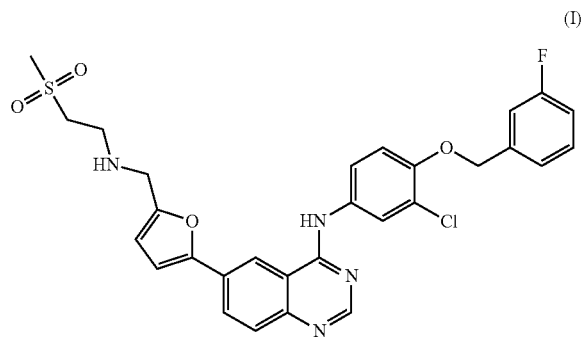 [SMILES: CS(=O)(=O)CCNCc1ccc(-c2ccc3ncnc(Nc4ccc(OCc5cccc(F)c5)c(Cl)c4)c3c2)o1]

or the pharmaceutically acceptable salt thereof, wherein the step of converting the compound of formula (X) comprises:
i) reacting the compound of formula (X):

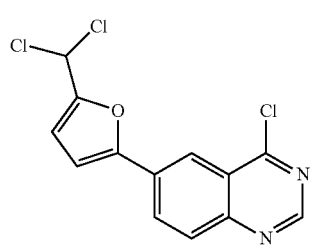

with a compound of formula (VII):

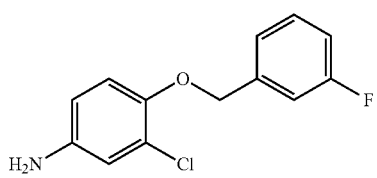

in a solvent to produce a compound of formula (IV) or its salt

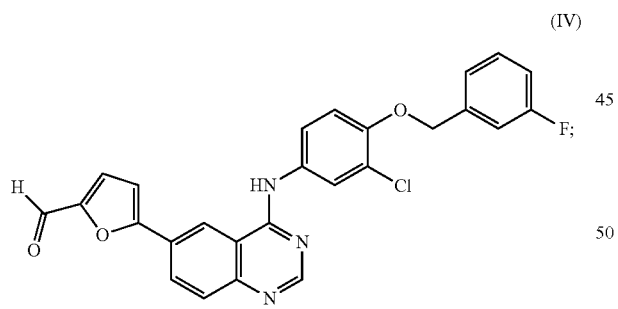

and
ii) reductively aminating the compound of formula (IV) or its salt with a compound of formula (VIII)

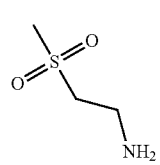

or its salt to provide lapatinib or the pharmaceutically acceptable salt thereof.

2. The process of claim 1 wherein the solvent is selected from the group consisting of tetrahydrofuran (THF), acetonitrile (MeCN), N,N-dimethylformamide (DMF), N,N-dimethylacetamide (DMAC), 1,3-dimethyl-2-imidazolidinone (DMI), N-methylpyrrolidone (NMP), tetramethylurea (TMU), and combinations thereof.

3. The process of claim 1 wherein the solvent is selected from THF, DMF, MeCN, each having a water content of no more than 100 ppm as determined by Karl-Fischer (KF) titration, and combinations thereof.

4. The process of claim 1 wherein the solvent is MeCN with a KF value of no more than 100 ppm.

5. The process of claim 1 further comprising a step of reacting laptinib with p-toluenesulfonic acid to produce lapatinib ditosylate.

6. A compound of formula (X):

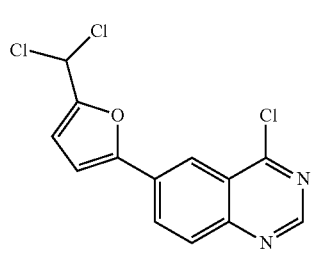

or a salt thereof.

7. The compound of claim 6 wherein the salt is a hydrochloric acid salt of the compound of formula (X).

8. A process for preparing a compound of formula (X):

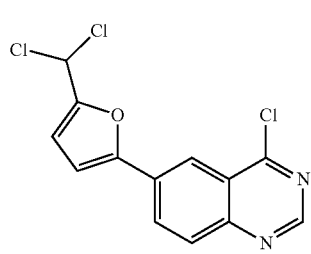

comprising a step of reacting a compound of formula (IX):

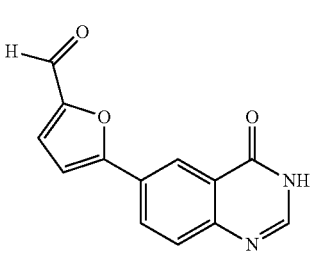

with SOCl$_2$ in the presence of toluene.

* * * * *